(12) United States Patent
Landry et al.

(10) Patent No.: US 6,442,814 B1
(45) Date of Patent: Sep. 3, 2002

(54) APPARATUS FOR MANUFACTURING A BONE DOWEL

(75) Inventors: Michael E. Landry; Erik J. Wagner, both of Austin, TX (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

(21) Appl. No.: 09/298,269

(22) Filed: Apr. 23, 1999

(51) Int. Cl.[7] .............................................. B23Q 37/00

(52) U.S. Cl. .......................... 29/26 B; 29/27 A; 408/20; 408/62; 408/102; 408/234; 409/65; 409/78; 409/165; 409/172; 409/198

(58) Field of Search .............................. 408/21, 20, 22, 408/23, 62, 64, 65, 89, 90, 91, 102, 234, 26, 24, 99, 100, 101, 103, 104, 108, 137; 29/26 A, 26 B, 27 A, 27 C; 409/131, 132, 72, 73, 76, 77, 163, 166, 167, 168, 165, 172, 185, 189, 198, 65, 66, 78; 623/901, 17

(56) References Cited

U.S. PATENT DOCUMENTS

| | | | |
|---|---|---|---|
| 1,358,040 A | * 11/1920 | Trundle, Jr. | 409/189 |
| 2,028,727 A | * 1/1936 | Perry et al. | 408/234 |
| 2,370,286 A | * 2/1945 | Berger | 408/234 |
| 2,378,302 A | * 6/1945 | Kline | 409/76 |
| 2,388,152 A | * 10/1945 | Jarvis et al. | 409/163 |
| 3,222,052 A | * 12/1965 | Freda | 408/91 |
| 3,470,789 A | * 10/1969 | Morse | 408/20 |
| 3,704,648 A | * 12/1972 | Burfoot | 409/76 |
| 3,848,601 A | 11/1974 | Ma et al. | |
| 3,988,814 A | 11/1976 | Hoffman | |
| 4,044,650 A | 8/1977 | Lyon et al. | |
| 4,057,893 A | 11/1977 | Smith et al. | |
| 4,401,112 A | 8/1983 | Rezaian | |
| 4,501,269 A | 2/1985 | Bagby | |
| 4,515,191 A | 5/1985 | Fetty | |
| 4,566,169 A | * 1/1986 | Vesely | 408/234 |
| 4,625,377 A | * 12/1986 | Kavthekar | 409/165 |

(List continued on next page.)

FOREIGN PATENT DOCUMENTS

| | | | | |
|---|---|---|---|---|
| DE | 43 23 956 | 10/1994 | | |
| EP | 0 260 044 | 3/1988 | | |
| EP | 0 307 241 | 3/1989 | | |
| ES | 9500308 | 2/1995 | | |
| FR | 2 717068 | 9/1995 | | |
| GB | 2025282 | * 1/1980 | | 29/26 A |
| JP | 86407 | * 4/1991 | | 29/27 C |
| SU | 1424826 | 9/1988 | | |
| WO | 88/06943 | * 9/1988 | | 29/27 C |
| WO | 97/00054 | 1/1997 | | |
| WO | 97/06753 | 2/1997 | | |
| WO | 98/17209 | 4/1998 | | |
| WO | 98/55052 | 12/1998 | | |

OTHER PUBLICATIONS

Albee et al., *Bone Graft Surgery in Disease, Injury and Deformity*, D. Appleton–Century Co., Inc., 1940, pp. xi–xv, 1–31, 48–107, and 210–227.

Vich, "Upgrade of the Cloward procedure: new instruments," J. Neurosurg., vol. 81, Nov. 1994, pp. 716–720.

Vich, "Anterior cervical interbody fusion with threaded cylindrical bone," J. Neurosurg., vol. 63, Nov. 1985, pp. 750–753.

"Introducing the EndoDowel™," Musculoskeletal Transplant Foundation, Oct. 1996.

Catalog from Musculoskeletal Transplant Foundation, Apr. 1996.

(List continued on next page.)

*Primary Examiner*—Daniel W. Howell
(74) *Attorney, Agent, or Firm*—Eric B. Meyertons; Conley, Rose & Tayon, P.C.

(57) ABSTRACT

Apparatus for manufacturing a bone dowel includes a machine base with tracks on a surface thereof. Modules configured to slide in the tracks may include a module for a high speed rotary tool, a collet module, a vise module and a threading module.

72 Claims, 9 Drawing Sheets

U.S. PATENT DOCUMENTS

| | | |
|---|---|---|
| 4,714,469 A | 12/1987 | Kenna |
| 4,719,676 A * | 1/1988 | Sansone ..................... 29/26 A |
| 4,743,146 A | 5/1988 | Khmelnitsky et al. |
| 4,743,256 A | 5/1988 | Brantigan |
| 4,777,713 A * | 10/1988 | Kitamura ..................... 29/27 C |
| 4,834,757 A | 5/1989 | Brantigan |
| 4,856,503 A | 8/1989 | Schelhas |
| 4,863,476 A | 9/1989 | Sheppard |
| 4,867,620 A | 9/1989 | Newman et al. |
| 4,877,020 A | 10/1989 | Vich |
| 4,878,915 A | 11/1989 | Brantigan |
| 4,904,261 A | 2/1990 | Dove et al. |
| 4,936,848 A | 6/1990 | Bagby |
| 4,950,296 A | 8/1990 | McIntyre |
| 4,961,740 A | 10/1990 | Ray et al. |
| 5,015,247 A | 5/1991 | Michelson |
| 5,015,255 A | 5/1991 | Kuslich |
| 5,026,373 A | 6/1991 | Ray et al. |
| 5,052,089 A * | 10/1991 | Gadaud et al. ............. 409/166 |
| 5,055,104 A | 10/1991 | Ray |
| 5,090,279 A | 2/1992 | Enzinger |
| 5,112,354 A | 5/1992 | Sires |
| 5,123,926 A | 6/1992 | Pisharodi |
| 5,147,402 A | 9/1992 | Bohler et al. |
| 5,171,278 A | 12/1992 | Pisharodi |
| 5,192,327 A | 3/1993 | Brantigan |
| 5,263,953 A | 11/1993 | Bagby |
| 5,301,405 A | 4/1994 | Maker |
| 5,306,307 A | 4/1994 | Senter et al. |
| 5,306,309 A | 4/1994 | Wagner et al. |
| 5,333,657 A | 8/1994 | Hart |
| 5,336,240 A | 8/1994 | Metzler et al. |
| 5,370,697 A | 12/1994 | Baumgartner |
| 5,390,683 A | 2/1995 | Pisharodi |
| 5,397,364 A | 3/1995 | Kozak et al. |
| 5,425,772 A | 6/1995 | Brantigan |
| 5,443,514 A | 8/1995 | Steffee |
| 5,458,638 A | 10/1995 | Kuslich et al. |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,522,899 A | 6/1996 | Michelson |
| 5,536,271 A | 7/1996 | Daly et al. |
| 5,571,195 A | 11/1996 | Schönhöffer |
| 5,593,409 A | 1/1997 | Michelson |
| 5,601,556 A | 2/1997 | Pisharodi |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,598 A | 7/1997 | Brosnahan, III |
| 5,653,763 A | 8/1997 | Errico et al. |
| 5,658,337 A | 8/1997 | Kohrs et al. |
| 5,665,122 A | 9/1997 | Kambin |
| 5,669,909 A | 9/1997 | Zdeblick et al. |
| 5,776,199 A | 7/1998 | Michelson |
| 5,785,710 A | 7/1998 | Michelson |
| 5,797,917 A | 8/1998 | Boyd et al. |
| 5,814,084 A | 9/1998 | Grivas et al. |
| 5,964,016 A * | 10/1999 | Ito et al. ..................... 29/27 C |
| 6,096,081 A | 8/2000 | Grivas et al. |
| 6,095,728 A | 9/2000 | Howie |
| 6,131,259 A | 10/2000 | Stark et al. |
| 6,155,756 A | 12/2000 | Mericle et al. |
| 6,231,577 B1 | 5/2001 | Canedy |

OTHER PUBLICATIONS

"The MTF EndoDowel™," Musculoskeletal Transplant Foundation, 1996.
"Laparoscopic Bone Dowel Instruments," Sofamor Danek, 1995.
"Laparoscopic Bone Dowel Surgical Technique," Sofamor Danek, 1995.
Brantigan et al, "A Carbon Fiber Implant to Aid Interbody Lumbar Fusion (Mechanical Testing)," Spine, vol. 16, No. 6 Supplement, 1991).
"Trends in Spine & Disc Surger," MedPro Month, Nov. 1996.
Wittenberg et al., "Compressive Strength of Autologous and Allogenous Bone Grafts for Thoracolumbar and Cervical Spine Fusion," Spine, vol. 15, No. 10, 1990, pp. 1073–1078.
"Spinal Fusion Surgery and The BAK™ Interbody Fusion System," Spine Tech, Inc., 1993.
"BAK®/Cervical Interbody Fusion System," Spine Tech, Inc., 1994.
"The BAK™ Interbody Fusion System," Spine Tech, Inc., 1996.
"BAK™ Interbody Fusion System (Porosity)," Spine Tech, Inc., 1996.
"BAK™ Interbody Fusion System (Biomechanics)," Spine Tech, Inc., 1996.
"BAK™ Interbody Fusion System (Instrumentation)," Spine Tech, Inc., 1996.
"Bone Harvester," Spine Tech, Inc., 1996.
"Biomechanical Rationale, The BAK™ Interbody Fusion System: An Innovative Solution," Spine Tech, Inc., 1994.
"Surgical Technique using Bone Dowel Instrumentation, for Anterior Approach," Sofamor Danek, 1996.
"Surgical Technique using Bone Dowel Instrumentation, for Posterior Approach," Sofamor Danek, 1996.
Catalog from Cloward® Instruments, 1996.
White et al., Clinical Biomechanics of the Spine, J.B. Lippincott Co., 1978, White et al., 1990, pp. 551–552.
Hochschuler et al, "Compressive Strength of Hollow, Allograft Bone Cylinders Proposed for Lumbar Interbody Fusion," NASS 8th Annual Meeting, Oct. 1993.
"MD–I™ and MD–II™ Custom Machined Cortical Dowels," University of Florida Tissue Bank, 1996.
"MD–III™ Threaded Cortical Dowel, Design Rationale and Surgical Technique," University of Florida Tissue Bank, 1997.
"Operative Treatment of Degenerative Cervical Disk Disease," Journal of the Southern Orthopaedic Association, 1996.
"Ray Threaded Fusion Cage, Surgical Technique Manual," Surgical Dynamics, 1996.
"Ray Threaded Fusion Cage," Surgical Dynamics, 1996.
"Surgeons First in Region to Use Lumbar Cage for Spinal Disc Disease," Hohmann Enterprises, 1996.
Heim et al, "The Treatment of Lumbar Degenerative Motion Segment Pain," Spinal Frontiers, Jun. 1997.
"Threaded Bone Dowel," Hohmann Enterprises, 1997.
Technical Monograph, Threaded Cortical Dowel, "Mechanical Characteristics and Evaluation," University of Florida Tissue Bank, 1996.
"Tyler Neurosurgeon Jon T. Ledlie, MD, Introduces Bone Dowel Procedures for East Texas–Area Back Pain Sufferers," Tyler Neurosurgical Assoc., 1998.
"Tyler Neurosurgeon Jon T. Ledlie, MD, Introduces Laparoscopic Procedure for East Texas Back Pain Sufferers," Tyler Neurosurgical Assoc., 1998.
"Vertigraft™ Textured Allograft Bone Graft," LifeNet, 1998.
"New Approaches to Spine Surgery," USC University Hospital Quarterly, vol. 10, No. 3, 1998.
Beadling, "FDA clears spinal cages for interbody lumbar fusion," Orthopedics Today, vol. 16, No. 10, Oct. 1996, pp. 24–25.
International Search Report, Application No. PCT/US98/08832, mailed Sep. 1, 1998.

* cited by examiner

APPARATUS FOR MANUFACTURING A BONE DOWEL

BACKGROUND OF THE INVENTION

1. Field of the Invention

The present invention is related to the field of bone dowels, and more specifically designed to be used in a sterilized setting to manufacture a bone dowel for use in spinal surgery.

2. Description of the Relevant Art

Clinical spinal fusion procedures using bone graft have been used since as early as 1911 (Albee, JAMA 57:885–886, 1911). Anterior cervical interbody fusion with cylindrical smooth bone grafts as spacers was reported by several authors by the mid-1950's. In 1985, threaded cylindrical bone dowels were reported by Vich, (J. Neurosurg. 63:750–753, 1985), eliminating the need to hammer the dowels in place. In the use of these dowels, a cylindrical bed was drilled in the appropriate intervertebral bodies and the graft was then screwed into the opening. Bone grafts could be attained from iliac crests as described by Cloward, (J. Neurosurg. 15:602–617, 1958; Clin. Neurosurg. 8:93–132, 1962) or using a Kiel-surgibone heterologous graft (Vich, 1985). Threaded dowels were prepared with a sterilized die or with a small lathe.

U.S. Pat. No. 5,814,084 describes cortical bone dowels derived from cortices of bone diaphyses that may have a chamfered insertion end. The dowels described in the '084 patent may also include a canal derived from the intramedullary space of a diaphysial bone that retains the natural architecture of that region of the bone, and which can be packed with cancellous bone. The background section of U.S. Pat. No. 5,814,084 provides a discussion of the development of the art and is incorporated herein by reference.

SUMMARY OF THE INVENTION

The present disclosure is directed to devices and methods for manufacturing a bone dowel. A device for manufacturing a bone dowel as disclosed herein may include a machine base with two or more tracks in a surface thereof, and at least one track may be perpendicular to at least one other track. In this configuration, the machine base may include at least one perpendicular intersection of two or more tracks. The device may also include a rotary cutting tool module, configured to hold a rotary cutting tool and to slide in a track in the machine base. The device may also include one or more modules for holding a dowel, preferably configured such that the modules are configured to slide in the tracks in both parallel and perpendicular orientation to a rotary cutting tool module disposed in a track during use, thus enabling an operator to perform various cutting, drilling and milling operations on a dowel.

As is described herein, one or more modules may slide in the tracks in perpendicular or parallel orientation to a cutting tool during use. Although embodiments are described in which a machine base contains two tracks in perpendicular orientation, a machine base may also contain two, three, or more tracks perpendicular to one or more tracks that may be configured to hold a cutting tool module, for example. In this way, more than one dowel module may be disposed on the machine base simultaneously or even sequentially in different tracks as needed to contact one or more cutting tools.

In one embodiment, a device for manufacturing a bone dowel in which a rotary cutting tool may be held in an appropriate position, and a module holding a dowel may be moved relative to the cutting tool in order to contact the rotary tool and shape the dowel to the desired size and configuration is described. In other embodiments, both the cutting tool and the dowel are held in modules that slide in tracks for controlled positioning and machining of the dowel.

The devices disclosed herein offer certain advantages over more conventional dowel manufacturing devices, such as lathes, in which a motor is connected to a shaft or other device configured to turn the dowel, and an operator then contacts the dowel with a knife, a gouge, or other stationary tool. Dowels made on such a device are typically machined to size in a clean room and then a number of different sizes are packaged and frozen. A surgeon typically thaws a number of different sizes of dowels so that one can be chosen during surgery that best fits the need of the patient. Unfortunately, the dowels that are not used cannot be re-frozen and must be discarded. The devices disclosed herein, in contrast, can be used in the operating room during surgery. The use of high speed rotary cutting tools is, in fact, routine in certain surgical procedures in operating rooms and the present device is adaptable to those rotary cutting tools. The present devices, then, may be sterilized and used in surgery to produce a dowel of the needed size from a blank, after the surgeon has determined the needed size. This reduces waste of human tissue and unnecessary expense, since only the single dowel blank need be thawed, rather than a selection of pre-sized dowels.

In certain embodiments, the modules for holding a dowel include a collet module, including a base configured to slide in a track and a collet configured to hold a dowel such that an end of the dowel can contact the cutting tool during use. A collet may be configured to hold a dowel by one end such that the opposite end may contact the cutting tool. As used herein, a dowel may typically be cylindrically shaped, such that the dowel is defined by two ends separated by the height of the dowel. The height may also be described as the long axis of the dowel, and the circumference of the long axis as the circumferential portion of the dowel. A collet module may be configured to hold a dowel parallel to the base of the module, or perpendicular to the base. As described herein, parallel means that the long axis of the dowel is parallel with the track in which the base is held during use. In some embodiments, a collet module is particularly useful to machine an end of a dowel smooth by moving a dowel in a track perpendicular to the rotary cutting tool until an end contacts the cutting tool burr. The dowel may then be manually rotated to achieve a smooth end. The collet module may also be particularly useful for drilling a center hole in an end of a dowel by moving the dowel in parallel orientation to a drill bit mounted on a rotary cutting tool held in a rotary tool module.

The modules for holding a dowel may also include a vise module including a base configured to slide in a track and a vise configured to hold a dowel along the length thereof such that an end of the dowel can contact a cutting tool during use. A vise module may include an opposed pair of jaw members configured to move together to press against an object held between the jaw members. In some embodiments, vise modules may include a groove or indention in one or both jaw members configured to conform to the circumferential portion, or the sides of the long axis of a dowel. The module may preferably be configured to hold a dowel perpendicular to the base such that an end of the dowel is free to be machined during use. The vise module may also be configured to hold a dowel securely against a force resulting from a cutting tool traveling across the face of an end. The vise module is particularly useful in cutting a groove into an end of a dowel. Such a groove may be useful for orienting a dowel during surgery, or for interacting with a tool used to insert the dowel into a spine. As such, a dowel held in the vise module may be moved in a track perpendicular to a cutting tool to machine such a groove or slot during use.

A device for manufacturing a bone dowel may also include a threading module including a base configured to slide in a track, a dead center, and a chuck opposed to the dead center, configured to hold a dowel by the ends such that a cutting tool may contact the circumferential portion of the dowel during use. In certain embodiments, the chuck may be configured to hold the dowel by one end and may provide a mechanism for turning or rotating the dowel around its long axis. In other embodiments, a dead center is provided that may engage a center hole drilled in the opposite end of a dowel during a previous step in manufacture, and the dead center may be spring loaded to hold the dowel in the module during use. In some embodiments, a coil spring is used, but other spring configurations may also be used to bias the dead center toward the chuck of the module.

In certain embodiments, a device for manufacturing a bone dowel may include a support member attached to the machine base in a track, wherein the support member includes a threaded opening. The support member may be disposed at an end of a track that is perpendicular to a track containing a cutting tool module, or it may be disposed anywhere in a perpendicular track, or even in parallel orientation to the cutting tool module. The threaded opening may be configured to engage a threaded projection included on certain modules, configured such that turning the threaded projection in the threaded opening is effective to move the module in the track. In this way an operator has better control of the module than is possible with a free-hand movement of the module. For example, a collet module may include a threaded projection configured to threadably mate with the threaded opening such that turning the threaded projection is effective to move the collet module in the track. The collet module may also include a knob attached to the threaded projection configured so that turning the knob turns the threaded projection. In certain embodiments a threading module may also include a threaded projection configured to threadably mate with the threaded opening such that turning the threaded projection is effective to move the threading module in the track, and to turn a dowel held in the threading module. In this way, an operator may make more than one pass with the threading module while maintaining the starting point and pitch in order to cut threads into a dowel. This embodiment is particularly preferred for threading a dowel, because of the ease of returning to the start of a thread. The pitch of the threaded opening also determines the pitch of the threads cut on a dowel.

The module for holding a rotary cutting tool as used in any of the described devices may be disposed in a track and may include an arm rigidly attached to the module and configured to threadably engage a threaded rod. In certain embodiments, a threaded rod may be provided and disposed parallel to the track holding the rotary cutting tool module. In some embodiments, the rod is rotatable and may be held in one or more support members attached to the machine base. In this configuration, turning the rod is effective to move the cutting tool module in the track. A knob may be attached to the rod to aid an operator in turning the rod. Any of the devices described herein may further include a high speed rotary cutting tool.

Described herein are also methods of manufacturing a bone dowel. Methods may include: providing a machine base including two or more tracks, wherein at least one track is perpendicular to at least one other track; providing a rotary cutting tool module in a first track and further providing a rotary cutting tool held in the module; providing one or more modules for holding a dowel, wherein the modules are configured to slide in the tracks in both parallel and perpendicular orientation to the first track; providing a bone dowel; moving the bone dowel past the cutting tool and in contact with a burr mounted on the cutting tool by sliding a module holding the dowel past the cutting tool when the module is in a second track, perpendicular to the first track, or by sliding a module toward the cutting tool when the module is in the first track. In some embodiments, the modules for holding a dowel may include a collet module including a base configured to slide in a track and a collet configured to hold a dowel such that an end of the dowel can contact the cutting tool during use; a vise module including a base configured to slide in a track and a vise configured to hold a dowel along the length thereof such that an end of the dowel can contact a cutting tool during use; and a threading module including a base configured to slide in a track, a dead center, and a chuck opposed to the dead center, configured such that a dowel held in the threading module can contact a cutting tool while rotating around the long axis of the dowel during use.

Methods may also include providing a support member attached to the machine base in a track, wherein the support member includes a threaded opening, and may further include providing a support member including a threaded opening attached to the machine base in a track, and wherein the collet module includes a threaded projection configured to threadably mate with the threaded opening such that turning the threaded projection is effective to move the collet module in the track. In addition, some embodiments may include providing a support member including a threaded opening attached to the machine base in a track, and wherein the threading module includes a threaded projection configured to threadably mate with the threaded opening such that turning the threaded projection is effective to move the threading module in the track, and to turn a dowel held in the threading module. In the practice of some embodiments, the module for holding a rotary cutting tool may be disposed in a track and include an arm rigidly attached to the module and configured to threadably engage a threaded rod, wherein the rod may be disposed parallel to the track and may be rotatable in one or more support members attached to the machine base such that turning the rod may be effective to move the module in the track.

Some embodiments of manufacturing a bone dowel as described herein may also include placing a collet module in a second track, perpendicular to a first track, and securing the bone dowel in the collet module; mounting a cutting tool burr on the cutting tool; moving the cutting tool module to position the cutting tool burr parallel with the end of the dowel; moving the collet module to contact the cutting tool burr effective to smooth the first end of the dowel; flipping the dowel in the collet and moving the collet module to contact the cutting tool burr effective to smooth the second end of the dowel; mounting a bit in the cutting tool; moving the collet module to the first track; moving the collet module to contact the cutting tool bit effective to drill a centered hole in the end of the dowel; flipping the dowel in the collet and moving the collet module to contact the cutting tool burr effective to drill a centered hole in the opposite end of the dowel.

The methods may also include: mounting a cutting tool burr in the cutting tool; placing a vise module in a track perpendicular to the first track; securing the dowel in the vise module; moving the cutting tool module to position the cutting tool burr parallel with the end of the dowel; moving the vise module past the cutting tool effective to machine a groove in an end of the dowel. The methods may also include mounting a threading burr on the cutting tool; placing a threading module in a track perpendicular to the first track; mounting the dowel in the threading module; positioning the modules so that the burr contacts the dowel near one end thereof, and simultaneously turning the dowel and sliding the threading module past the cutting tool effective to thread the dowel.

Also disclosed herein are methods of manufacturing a device for manufacturing a bone dowel, including: manufacturing a machine base including two or more tracks, wherein at least one track is perpendicular to at least one other track; manufacturing a rotary cutting tool module, wherein the module is configured to hold a rotary cutting tool and to slide in a track; and providing one or more modules for holding a dowel, wherein the modules are configured to slide in the tracks in both parallel and perpendicular orientation to a rotary cutting tool module disposed in a track during use. In some embodiments, the modules for holding a dowel may include a collet module including a base configured to slide in a track and a collet configured to hold a dowel such that an end of the dowel can contact the cutting tool during use; a vise module including a base configured to slide in a track and a vise configured to hold a dowel along the length thereof such that an end of the dowel can contact a cutting tool during use; and a threading module including a base configured to slide in a track, a dead center, and a chuck opposed to the dead center, configured such that a dowel held in the threading module can contact a cutting tool while rotating around the long axis of the dowel during use.

The present disclosure also includes bone dowels manufactured by the methods and/or utilizing the devices described herein. Such dowels may also include dowels in which the canal formed by the intramedullary space has been improved by the removal of cancellous bone promoter better bone grafting of a dowel to the adjacent vertebrae.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
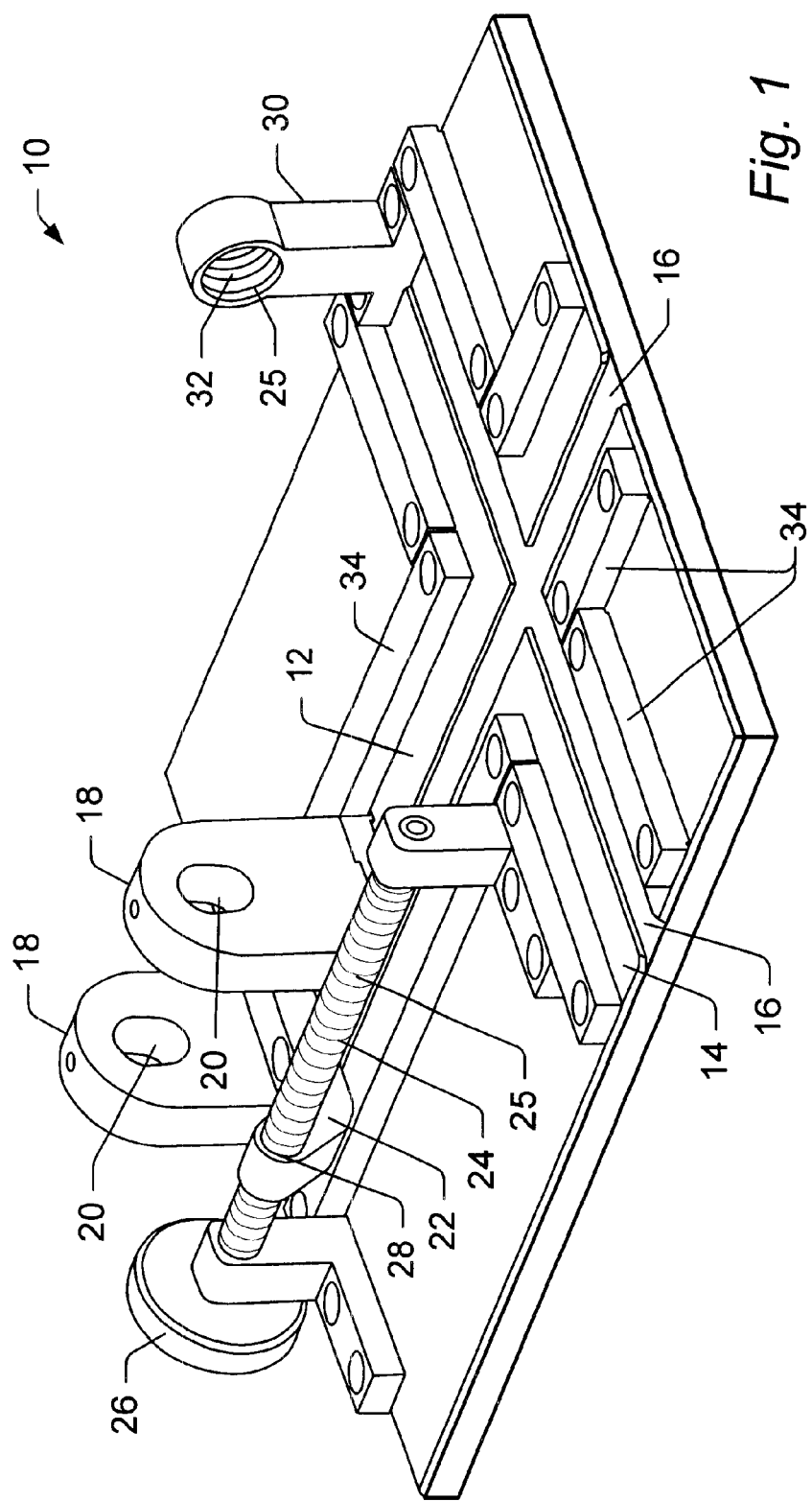
FIG. 1 depicts a machine base without cutting tools or modules.

An embodiment of a machine base 10 without cutting tools or modules is shown in FIG. 1. The machine base shown includes perpendicular tracks defined by rails 34, including a cutting tool track 12 and a track for the working modules 14 that intersect to form a cross shape. Both tracks contain a groove 16 to guide the motion of the various modules in the tracks. The machine base as shown in FIG. 1 also includes a cutting tool module 18 configured to hold a standard high speed cutting tool. Such tools may be obtained from Dremel of Racine, Wis., for example. In the embodiment shown, the tool lies horizontally in the openings 20. The cutting tool module 18 is shown connected by an arm member 22 to a bar or rod 24. The bar 24 is shown attached to a knob 26. In the embodiment shown, bar 24 may be threaded with threads 25 and may be configured to mate with threads in an opening 28 in the end of arm member 22. In this configuration, turning knob 26 is effective to move the cutting tool module 18 along the track 12, and to thus move the cutting tool toward or away from a dowel during use. The embodiment shown also includes a support member 30 having an opening 32 therethrough, which may in certain embodiments be a threaded opening configured with threads 25 to accept an extension, or a threaded extension of a working module during use.

Figure 2:
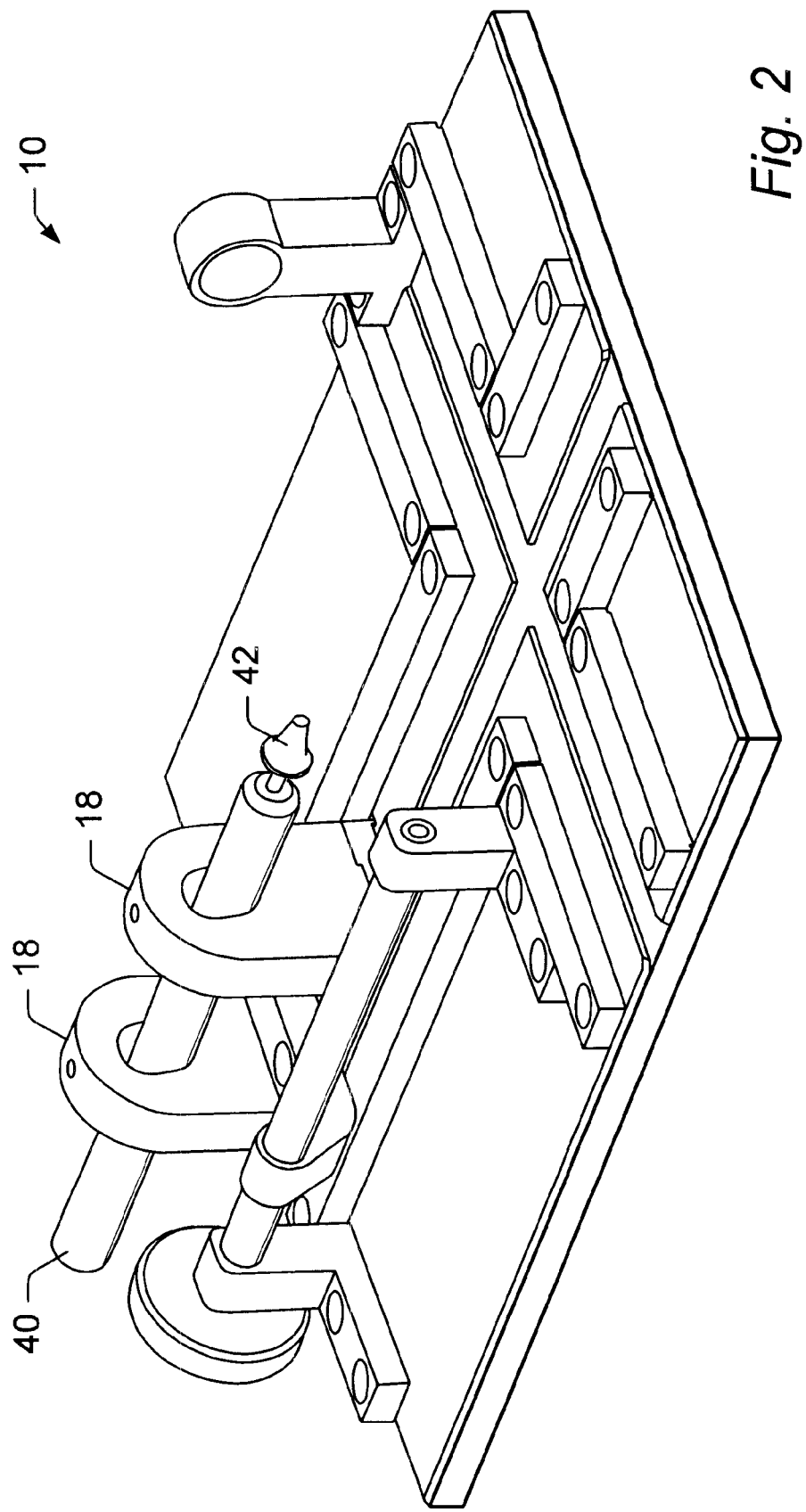
FIG. 2 depicts a machine base with a cutting tool.

A machine base 10 with a cutting tool 40 held in the cutting tool module 18 is shown in FIG. 2. Typically, the cutting tool 40 is connected to a switched motor by a cable (not shown) configured to turn a shaft in the tool 40 at high speed. Shown mounted on the cutting tool 40 is a burr or bit 42 for working the dowel.

Figure 3:
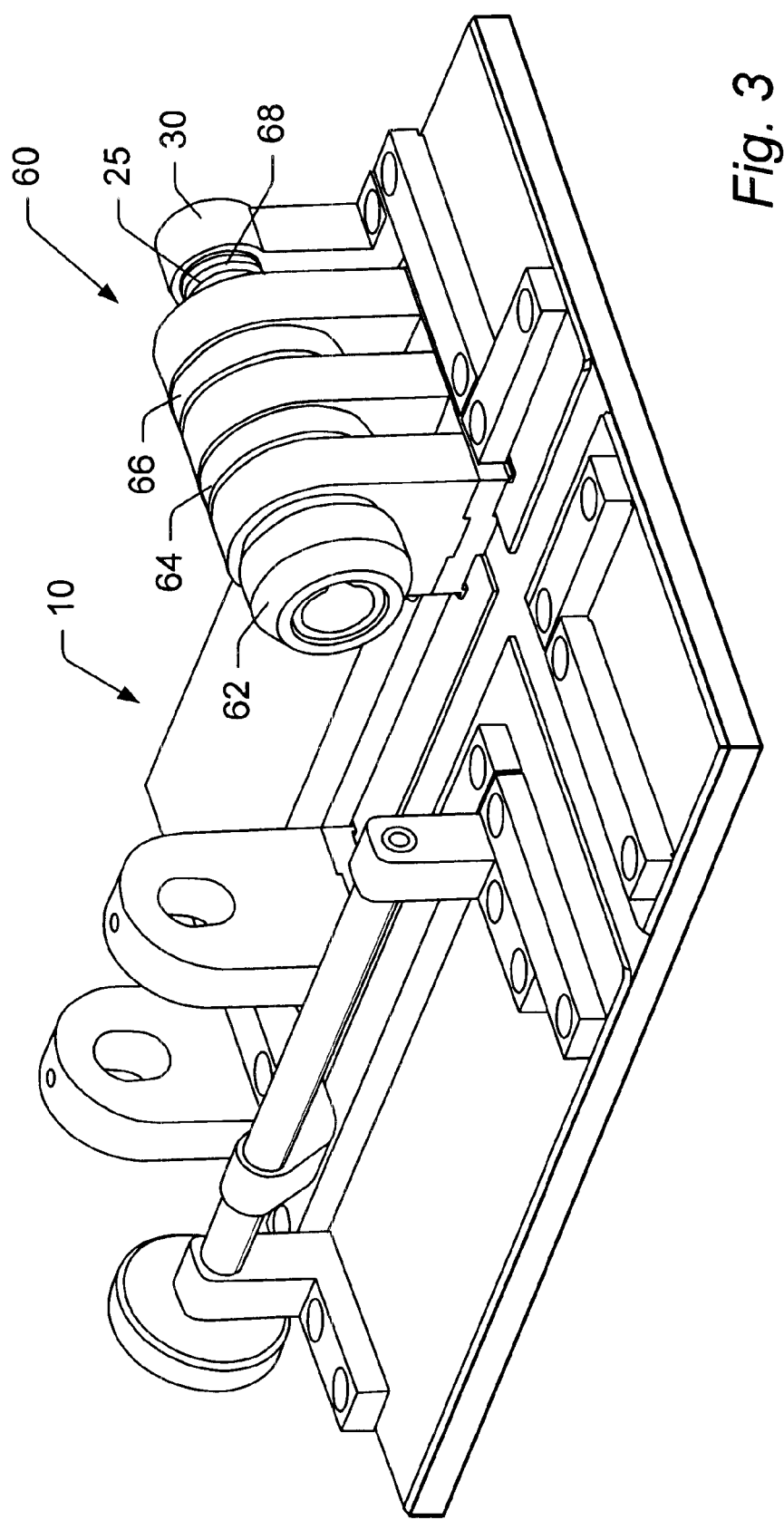
FIG. 3 depicts a machine base with a collet module in the perpendicular position.
Figure 7:
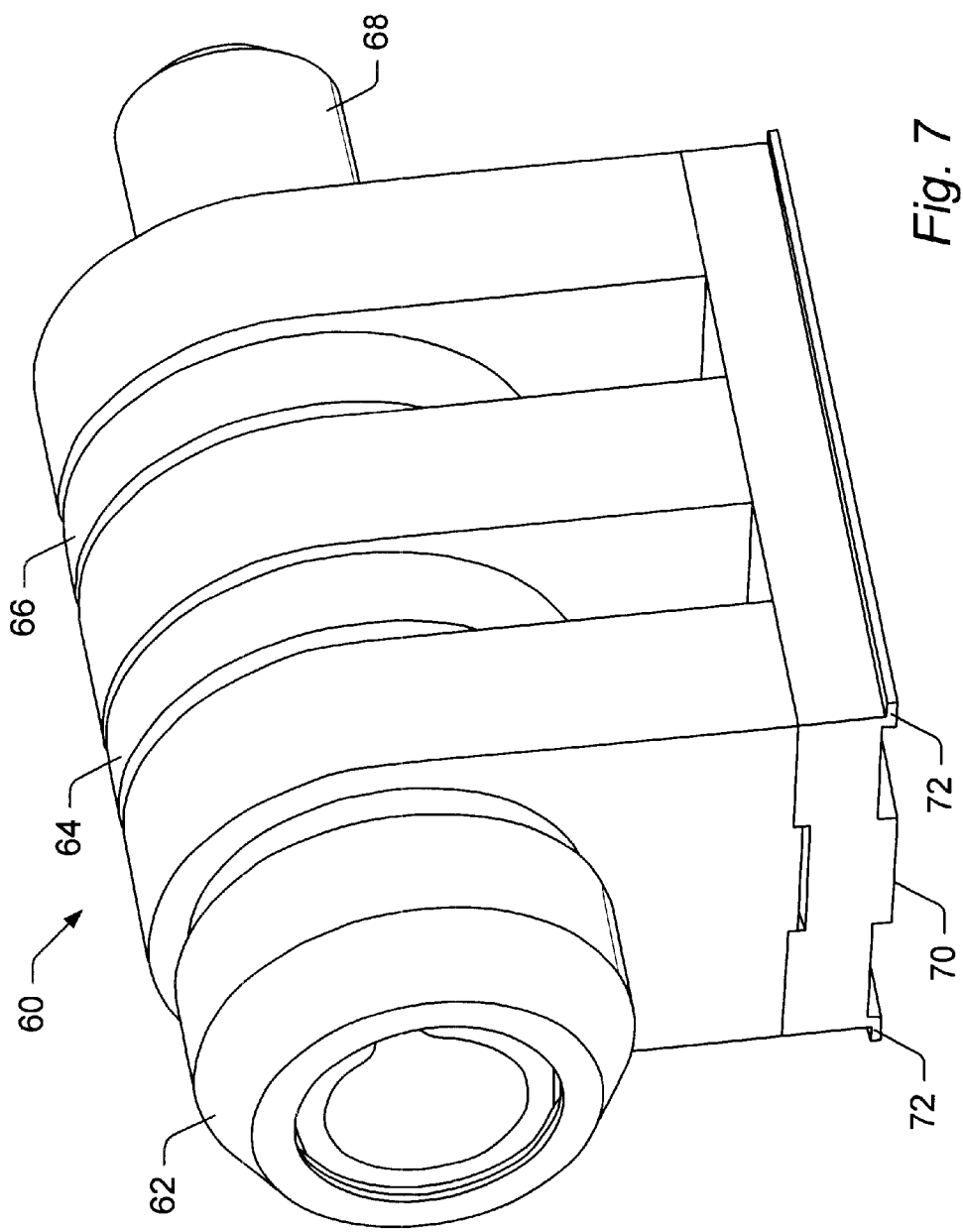
FIG. 7 depicts a collet module.

A machine base 10 with a collet module 60 in the perpendicular position is shown in FIG. 3. A collect module 60 is also shown in isolation in FIG. 7. The collect module includes a collect 62 configured to hold a bone dowel. A knob 64 may be connected to the collect 62 such that turning the knob turns the collect 62 and thus a dowel held in the collet 62. A second knob 66 may be connected to an extension 68, preferably a threaded extension with threads 25. As shown in FIG. 3, extension 68 may be received by support member 30, such that when the extension 68 and the opening 32 include mating threading, turning of knob 66 is effective to move the collet module 60 along the track 14, thus moving a dowel held in collect 62 perpendicular to a cutting tool 40 during use. Also shown in FIG. 7, the bottom to the collet module may include a projection 70 configured to ride in grooves 16 within tracks 12 and 14 of machine base 10. Also shown are flanges 72, configured to mate with rails 34. This configuration allows precise, controlled movement of the modules through the tracks.

Figure 4:
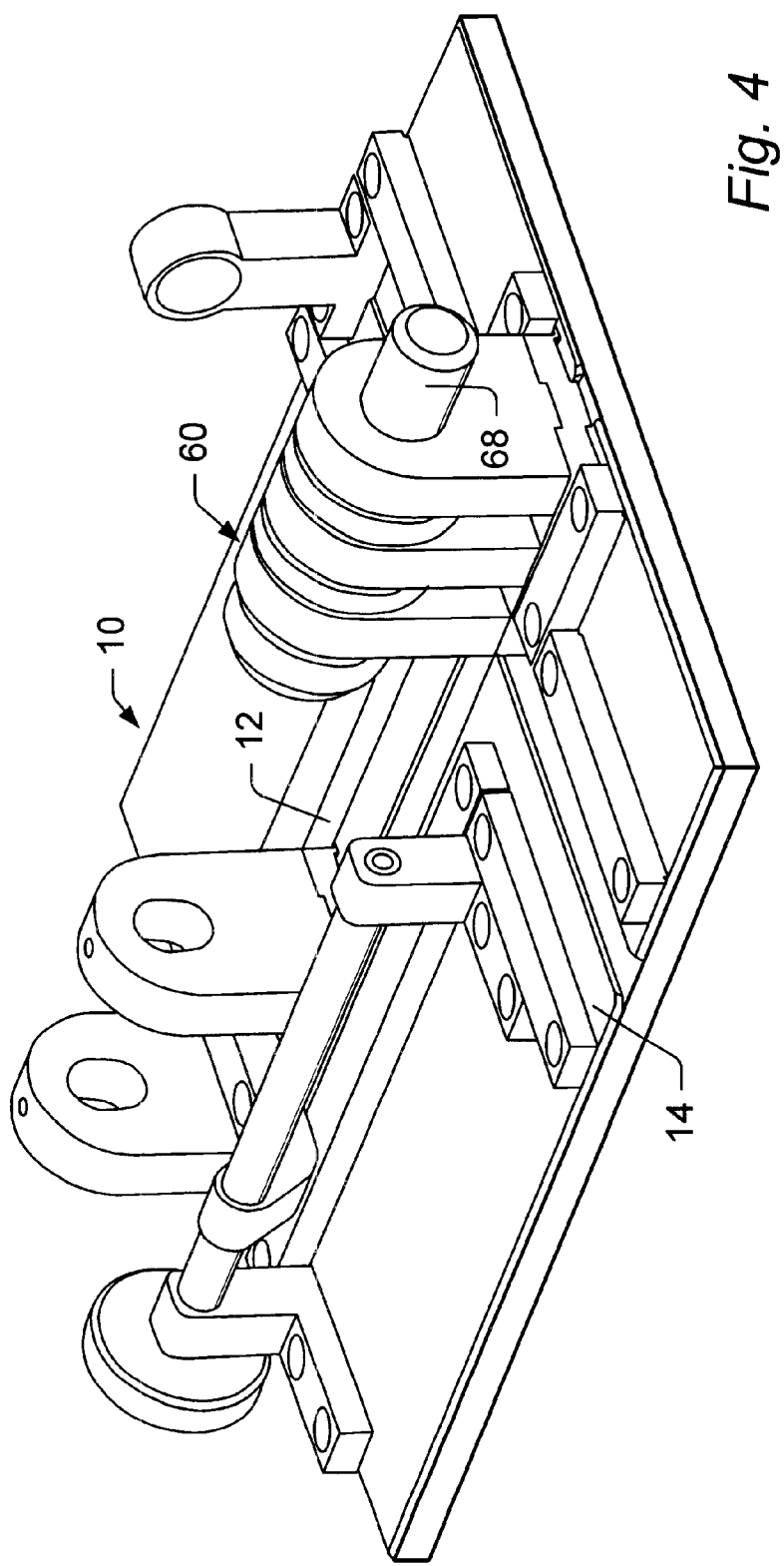
FIG. 4 depicts a machine base with a collet module in the parallel position.

During the manufacture of a bone dowel, the collet module is most useful for holding a dowel by one end while smoothing and drilling holes in the opposite end of the dowel. For example, a bone dowel may be held by one end in the collet with the collet module in the perpendicular orientation. Initially, the collet module may be positioned next to the support member, so that the dowel does not extend over the cutting tool track 12. The cutting tool module may be positioned such that the burr may extend over the track 14. During use, the cutting tool motor may be turned on so the burr is turning at high speed. By turning the knob 66 in the appropriate direction, the collet module 60 moves along the track 14 (perpendicular) until the dowel contacts the cutting tool burr, thus smoothing the end of the dowel. The collet module 60 may also be placed in the cutting tool track 12 (parallel orientation) such that the dowel may be pushed by hand directly into the turning burr or bit. This is the preferred method of drilling a hole in the end of a dowel during use. FIG. 4 depicts a machine base 10 with a collet module 60 in the parallel orientation as described. In the parallel orientation, the collet module 60 is preferably pushed along the track 12 by free hand, as the extension 68 is typically not engaged with a threaded opening.

Figure 5:
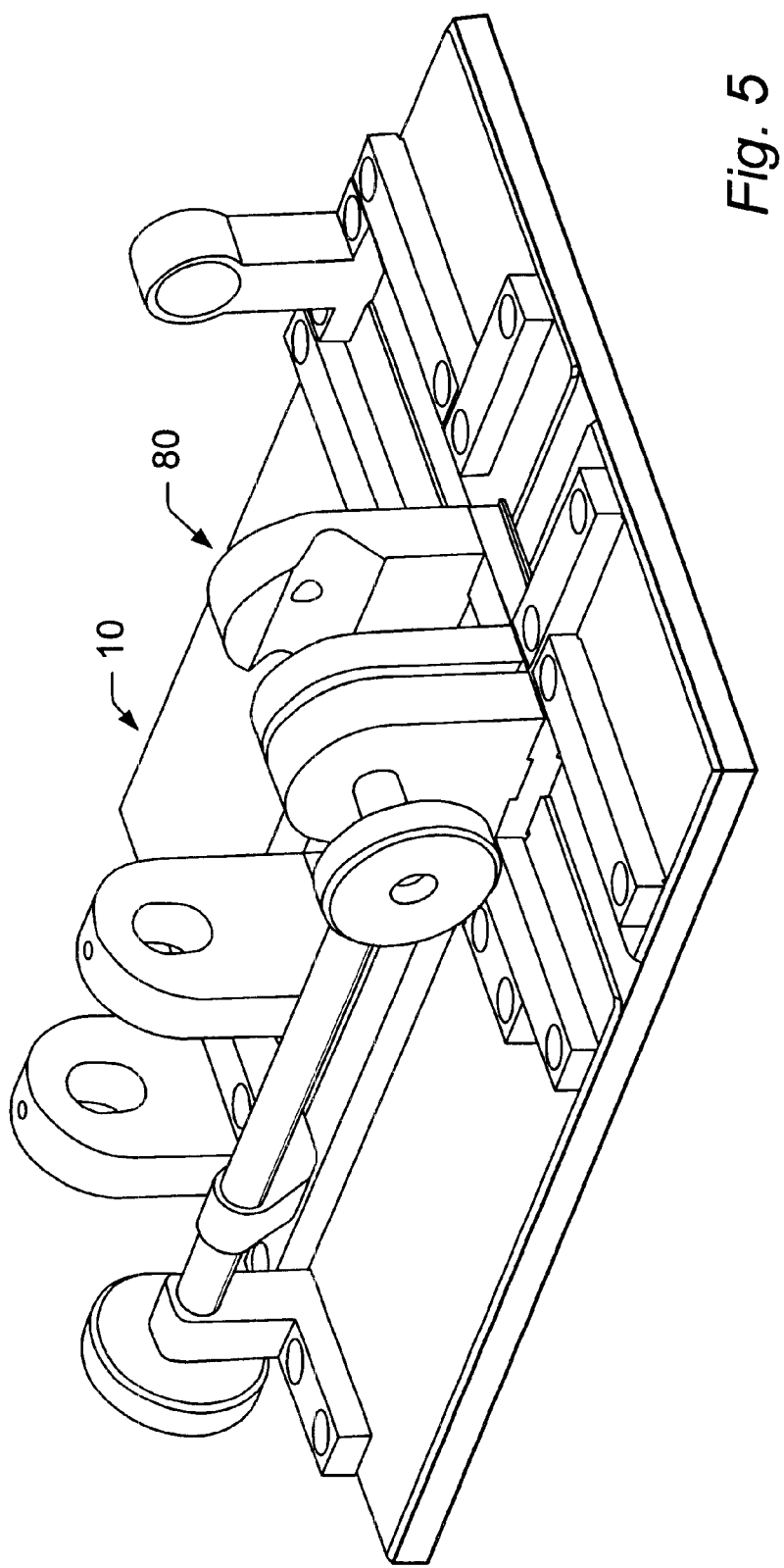
FIG. 5 depicts a machine base with a vise module.
Figure 8:
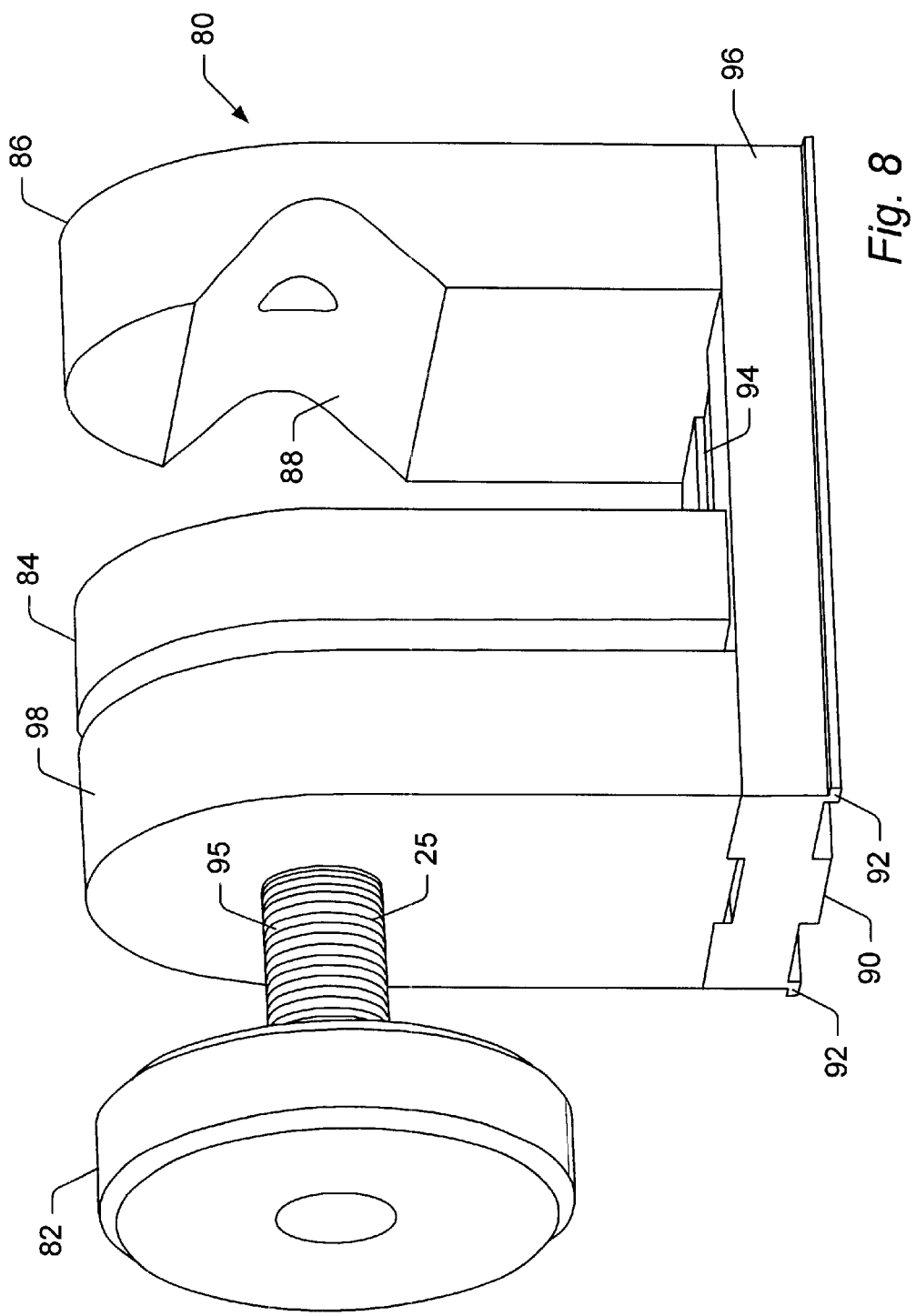
FIG. 8 depicts a vise module.

A machine base 10 with a vise module 80 is shown in FIG. 5. An example of a vise module 80 is shown in isolation in FIG. 8. The vise module 80 may be configured to hold a dowel so that an end of the dowel may be machined. Referring to FIG. 8, a vise module 80 may include a bottom as described for the collet module 60, including a projection 90 configured to ride in grooves 16 within tracks 12 and 14 of machine base 10. Also shown are flanges 92, configured to mate with rails 34. The bottom or base 96 of the vise module 80 may also include a track 94 on its top for a moveable vise jaw 84. The vise module 80 may also include a stationary vise jaw 86 that provides a groove 88 configured to hold one side of a dowel. The vise module 80 may also include a knob 82 connected to the moveable vise jaw 84 by a rod 95. The rod 95 may have threads 25. Support member 98 may provide a threaded opening, with threads that mate with threads on rod 95 such that turning knob 82 threads the rod 95 through the support member 98, thus moving the moveable jaw 84 until it contacts the stationary jaw 86, or a dowel held between the jaws of the vise. During use, a dowel may be held in the vise by force applied through turning of knob 82.

During manufacture of a bone dowel as described herein, the vise module 80 may be placed on the machine base 10 in the perpendicular orientation as shown in FIG. 5. A dowel may be placed in the vise and secured by turning knob 82 until the pressure of the jaws is sufficient to hold the dowel. Typically a cutting tool burr configured to produce a straight sided groove is mounted on the cutting tool and the tool is turned on. The vise module may then be moved past the cutting tool burr so that a groove is cut in the end of the dowel. The cutting tool module may then be moved closer to the vise module and the process repeated to deepen the groove as necessary. During surgical implantation of a dowel, such a groove is useful to mate with a screwdriver apparatus.

Figure 6:
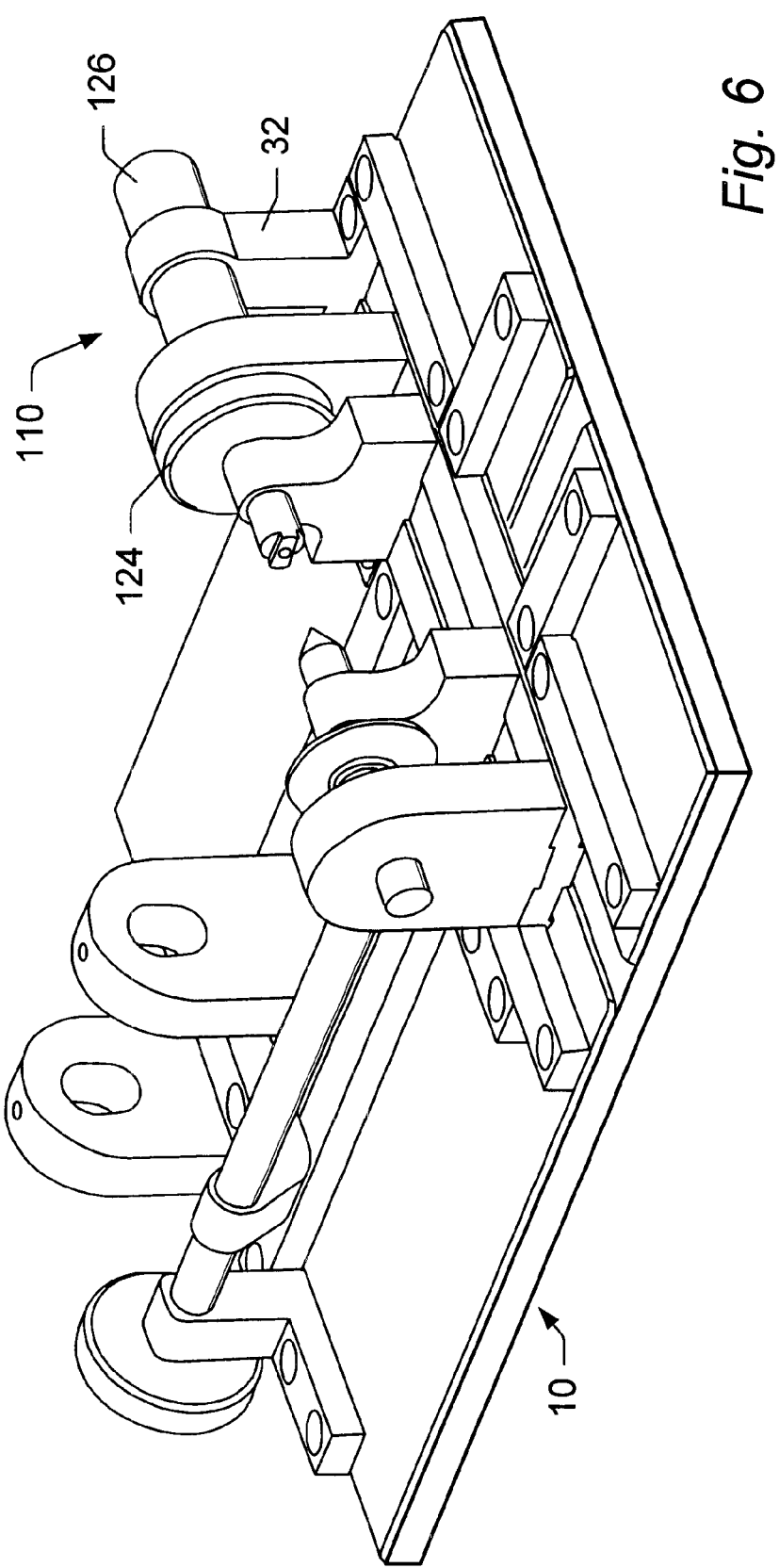
FIG. 6 depicts a machine base with a threading module.
Figure 9:
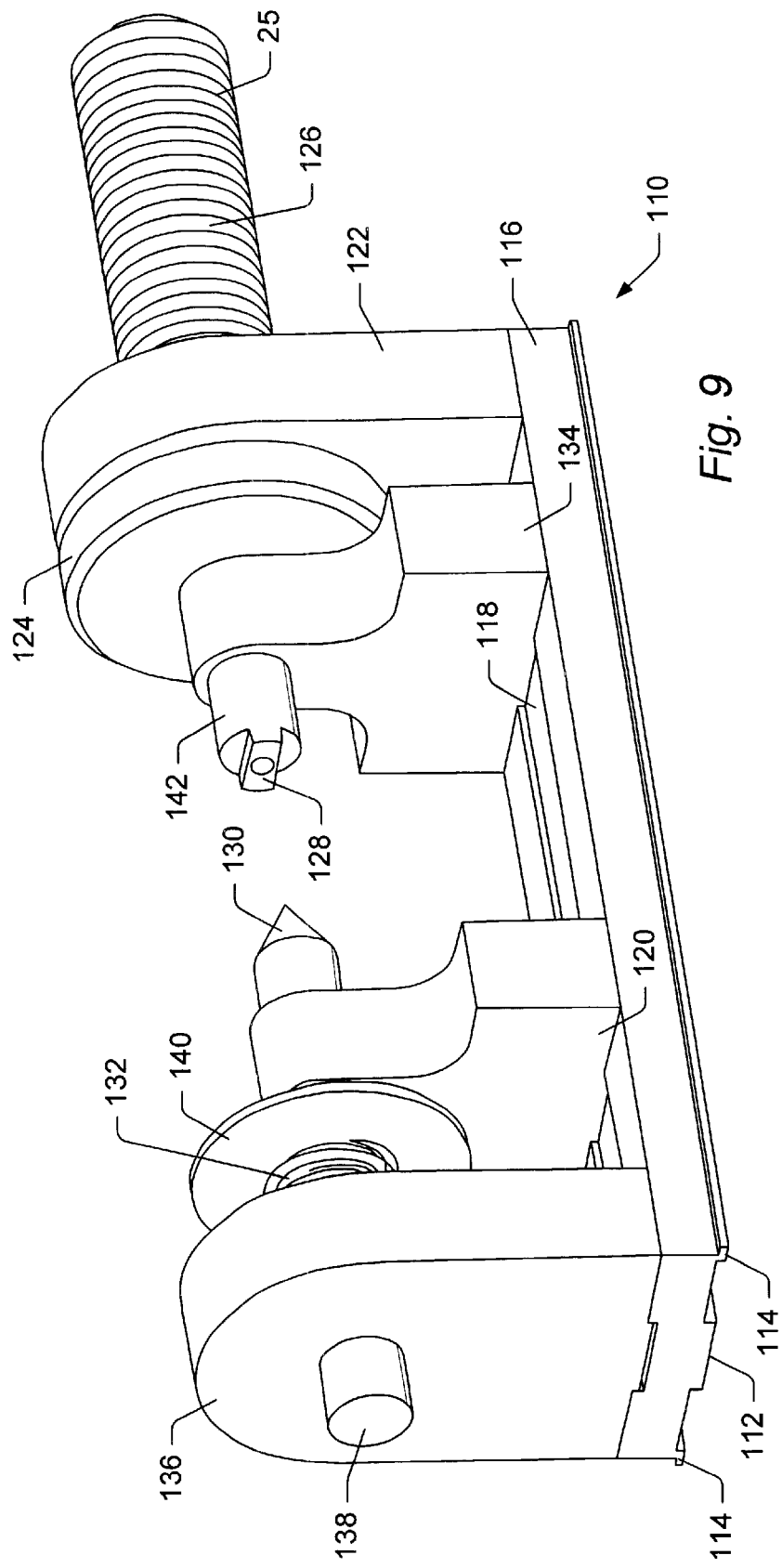
FIG. 9 depicts a threading module.

A machine base 10 with a threading module 110 in the perpendicular orientation is shown in FIG. 6. A threading module 110 is shown in isolation in FIG. 9. The bottom of base 116 of the threading module 110 may have the same configuration as the previously described modules including a projection 112 and flanges 114 for riding in the tracks 12, 14 of machine base 10. Base 116 may also provide a groove 118 for tracking of the moveable member 120 of the threading module 110. The module includes a first support member 136 that provides an opening for a rod 138 that may pass through support member 136 and a moveable member 120, and provide a dead center 130 configured to insert a point into a center hole drilled in the end of a dowel to be threaded. The rod 138 may be bonded to member 120 and may also pass through a spring 132 disposed between member 136 and 120 during use. In the described configuration, the spring biases moveable member 120 toward member 134. A disc 140 may also be attached to member 120 to provide a solid surface for spring 132.

A threading module 110 may also include an immobile support member 134 that provides a turning member or chuck 142 to hold a dowel to be threaded. As shown, a projection 128 may be provided to mate with a groove machined in an end of the dowel as described above. Also included in the embodiment of a threading module 110 is support member 122, which provides an opening for threaded projection 126. Threaded projection 126 may be configured with threads 25 to mate with the threaded opening 32 in support member 30 (FIG. 1). Threaded projection 126 may also be attached to a knob 124 configured such that turning the knob 124 is effective to thread the projection 126 through the opening 32. The knob 124 may also be attached to the chuck 142, such that turning the knob 124 also turns a dowel held by the chuck.

During use, the threading module may be placed on the machine base in the perpendicular orientation with projection 126 threaded through opening 32, and a dowel may be placed in the threading module. The end having a centered drilled hole may contact the dead center, and the grooved end may contact the other member 142 of the module. The spring may provide the tension to hold a dowel in place. A threading burr may be mounted on the cutting tool and the tool turned on. The cutting tool module may be moved toward the dowel by turning knob 26 as described above until the burr contacts the dowel. The burr may contact the dowel at one end of the dowel. While the burr contacts the dowel, an operator may turn knob 124, threading the projection through opening 32. This motion may serve to move the dowel past the burr and to simultaneously turn the dowel so that a thread is cut in the dowel. The threads in the dowel will thus have the same pitch as the threads in opening 32. The cutting tool may then be moved closer to the dowel and the process repeated to make deeper threads as needed.

Example of a Bone Dowel Manufacturing Procedure

The first step in a manufacturing procedure may be to determine the size of the first dowel. Donor bone may be first processed according to normal procedures of a bone tissue bank. The largest width of the medullary space may be measured and 6 mm may be added to this measurement to determine the smallest possible dowel that can be manufactured. The number may then be rounded up to the closest even number size (14, 16, 18, or 20 mm, for example). Using an oversized hole saw, (14.5, 16.5, 18.5, and 20.5 mm for this example), a cylindrical dowel may be cut from the ring, using care to ensure that the medullary space is centered in the dowel. The medullary space may be then deburred with a small file, and the dowel may be washed and stored.

The next step in processing the bone may be to determine the size of the remaining dowels. The largest width of the exposed medullary space may be measured and a ring may be cut with a width equal to this largest width plus 8 mm. The largest width of the exposed medullary space may be measured on both sides of the ring and 6 mm may be added to this number to determine the smallest possible dowel that can be manufactured from this ring. The number may be rounded up as above (14, 16, 18, or 20 mm, for example). If the number is smaller than 14 mm, then preferably no dowel is made from that ring. Using an oversized hole saw, a cylindrical dowel may be cut from the ring (14.5, 16.5, 18.5, and 20.5 mm for this example), using care to ensure that the medullary space is centered in the dowel. The medullary space may be then deburred with a small file, and the dowel may be washed and stored.

The dowels are then machined to length. First the length of the medullary space may be measured, 6 mm may be added to the measurement, and the number may be rounded up to determine the smallest possible dowel length (18, 22, or 26 mm, for example). The dowel may be cut with a band saw to 2 mm longer than the length determined as the smallest possible length for that dowel while centering the medullary space. The dowel may be then washed and stored.

The dowel prepared as described may be then ready for machining to its final shape. The machine base may be set up with the cutting tool in place and the burr attached. The dowel may be secured in the collet module, which may be placed in the base oriented perpendicular to the cutting tool. The distal end of the dowel may then be machined until smooth, removing no more than 1 mm. The collet may be then oriented parallel to the cutting tool and a pilot hole may be drilled in the center of the distal end of the dowel, using a drill bit. The dowel may be flipped in the collet module and the proximal end machined until smooth and a pilot hole drilled as was done to the distal end. The drilled pilot hole preferably penetrates to the medullary space.

A burr may then be placed on the cutting tool and the dowel may be placed in the vise module. The vise module may be placed in the machine base in the parallel orientation and a groove machined into the proximal end of the dowel.

The dowel may be next mounted in the threading module, which may be placed in the machine base in the perpendicular orientation. The dowel may be preferably mounted by supporting the pilot hole in the distal end of the dowel with the dead center and capturing the proximal end by the hole and groove. The thread cutting burr may be mounted on the cutting tool. Before cutting, the threading module may be moved into the base as far as possible. The cutting tool may be turned on and advanced until the burr touches the dowel. The knob on the threading module may then be turned until the entire dowel has moved past the burr. The threading module may then be returned to the starting position, the burr may be advanced approximately 0.020 inches, and the knob may be turned to move the dowel past the burr. The diameter of the dowel may then be measured using calipers, for example, and the process repeated until the desired diameter is achieved. The dowel may then be processed, packaged and stored according to normal tissue bank procedures, or it may be used in surgery immediately.

While the devices and methods of this disclosure have been described in terms of preferred embodiments, it will be apparent to those of skill in the art that variations may be applied to the devices, methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A device for manufacturing a bone dowel comprising:
    a machine base comprising two or more tracks, wherein at least one track is perpendicular to at least one other track;
    a rotary cutting tool module, wherein the module is configured to hold a rotary cutting tool and to slide in a track;
    at least one module for holding a dowel, wherein the at least one module is configured to slide in the tracks in both parallel and perpendicular orientation to a rotary cutting tool module disposed in a track during use; and
    wherein the at least one module for holding a dowel includes a collet module comprising a base configured to slide in a track and a collet configured to hold a dowel such that an end of the dowel can contact the cutting tool during use, wherein the collet module comprises a knob attached to the collet, and wherein the knob is configured to turn the collet when the knob is turned.

2. A device for manufacturing a bone dowel comprising:
    a machine base comprising two or more tracks, wherein at least one track is perpendicular to at least one other track;
    a module for holding a rotary cutting tool, wherein the module is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track;
    at least one module for holding a dowel, wherein the at least one module is configured to slide in the tracks in both parallel and perpendicular orientation to a rotary cutting tool module disposed in a track during use;
    wherein the at least one module includes a threading module comprising a base configured to slide in a track, a dead center, and a chuck opposed to the dead center, configured such that the circumferential portion of a dowel held in the threading module can contact a cutting tool while rotating around the long axis of the dowel during use; and
    wherein the machine base comprises a support member comprising a threaded opening attached to the machine base in a track, and wherein the threading module comprises a threaded projection configured to threadably mate with the threaded opening, such that turning the threaded projection is effective to move the threading module in the track and to turn a dowel held in the threading module.

3. The device of claim 1, wherein the at least one module is configured to hold the dowel parallel to the base.

4. The device of claim 1, wherein the at least one module includes a vise module comprising a base configured to slide in a track and a vise configured to hold a dowel along the length thereof such that an end of the dowel can contact a cutting tool during use.

5. The device of claim 4, wherein the at least one module is configured to hold a dowel perpendicular to the base.

6. The device of claim 1, wherein the at least one module includes a threading module comprising a base configured to slide in a track, a dead center, a threaded projection, and a chuck opposed to the dead center, and wherein the threading module is configured such that a dowel held in the threading module can contact a cutting tool while rotating around the long axis of the dowel during use.

7. The device of claim 1, wherein the device comprises a support member attached to the machine base in a track, wherein the support member comprises a threaded opening.

8. The device of claim 2, wherein the device is autoclavable.

9. A device for manufacturing a bone dowel comprising:
    a machine base comprising two or more tracks, wherein at least one track is perpendicular to at least one other track;
    a rotary cutting tool module, wherein the module is configured to hold a rotary cutting tool and to slide in a track;
    at least one module for holding a dowel, wherein the at least one module is configured to slide in the tracks in both parallel and perpendicular orientation to a rotary cutting tool module disposed in a track during use;

wherein the at least one module for holding a dowel includes a collet module comprising a base configured to slide in a track and a collet configured to hold a dowel such that an end of the dowel can contact the cutting tool during use;

a support member comprising a threaded opening attached to the machine base in a track; and wherein the collet module comprises a threaded projection configured to threadably mate with the threaded opening such that turning the threaded projection is effective to move the collet module in the track.

10. The device of claim 9, wherein the collet module comprises a knob attached to the threaded projection configured so that turning the knob turns the threaded projection.

11. The device of claim 9, wherein the device is autoclavable.

12. The device of claim 1, wherein the device is autoclavable.

13. The device of claim 1, further comprising a high speed rotary cutting tool.

14. The device of claim 1, wherein the module for holding a rotary cutting tool is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track.

15. The device of claim 14 further comprising a knob attached to the rod.

16. A device for manufacturing a bone dowel comprising:
a machine base comprising two or more tracks, wherein at least one track is perpendicular to at least one other track;
a module for holding a rotary cutting tool, wherein the module is configured to slide in the tracks;
a collet module comprising a base configured to slide in a track in both parallel and perpendicular orientation to a rotary cutting tool module, a collet configured to hold a dowel by one end thereof, and a knob attached to the collet configured so that turning the knob turns the collet;
a vise module comprising a base configured to slide in a track and a vise configured to hold a dowel along the length thereof; and
a threading module comprising a base configured to slide in a track, a dead center, and a chuck opposed to the dead center.

17. The device of claim 16, wherein the module for holding a rotary cutting tool is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track.

18. The device of claim 17 further comprising a knob attached to the rod.

19. The device of claim 16, further comprising a high speed rotary cutting tool.

20. The device of claim 16, wherein the device is autoclavable.

21. A device for manufacturing a bone dowel comprising:
a machine base comprising two or more tracks, wherein at least one track is perpendicular to at least one other track;
a module for holding a rotary cutting tool, wherein the module is configured to slide in the tracks;
a collet module comprising a base configured to slide in a track in both parallel and perpendicular orientation to a rotary cutting tool module and a collet configured to hold a dowel by one end thereof;
a vise module comprising a base configured to slide in a track and a vise configured to hold a dowel along the length thereof;
a threading module comprising a base configured to slide in a track, a dead center, and a chuck opposed to the dead center; and
a support member comprising a threaded opening attached to the machine base in a track, and wherein the collet module comprises a threaded projection configured to threadably mate with the threaded opening such that turning the threaded projection is effective to move the collet module in the track during use.

22. The device of claim 21, wherein the collet module is configured to hold a dowel such that an end of the dowel can contact a cutting tool disposed in a track in either parallel or perpendicular orientation during use.

23. The device of claim 21, wherein the vise module is configured to hold a dowel along the length thereof such that an end of the dowel can contact a cutting tool during use.

24. The device of claim 21, wherein the threading module is configured such that a circumferential portion of a dowel held in the threading module can contact a cutting tool while rotating around the long axis of the dowel during use.

25. The device of claim 21, further comprising a high speed rotary cutting tool.

26. The device of claim 21, wherein the device comprises a support member comprising a threaded opening attached to the machine base in a track.

27. The device of claim 9, further comprising a high speed rotary cutting tool.

28. The device of claim 21, wherein the collect module comprises a knob attached to the treaded projection configured so the turning the knob turns the threaded projection.

29. A device for manufacturing a bone dowel comprising:
a machine base comprising two or more tracks, wherein at least one track is perpendicular to at least one other track;
a rotary cutting tool module, wherein the module is configured to hold a rotary cutting tool and to slide in a track;
at least one module for holding a dowel, wherein the at least one module is configured to slide in the tracks in both parallel and perpendicular orientation to a rotary cutting tool module disposed in a track during use;
wherein the at least one module includes a threading module comprising a base configured to slide in a track, a dead center, a threaded projection, and a chuck opposed to the dead center, wherein the threading module is configured such that a dowel held in the threading module can contact a cutting tool while rotating around the long axis of the dowel during use; and
wherein the machine base comprises a support member comprising a threaded opening attached to the machine base in a track, and wherein the threading module comprises a threaded projection configured to threadably mate with the threaded opening such that turning the threaded projection is effective to move the threading module in the track, and to turn a dowel held in the threading module.

30. The device of claim 29, wherein the device is autoclavable.

31. The device of claim 21, wherein the device is autoclavable.

32. The device of claim 21, wherein the module for holding a rotary cutting tool is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track.

33. The device of claim 32 further comprising a knob attached to the rod.

34. A device for manufacturing a bone dowel comprising:
a machine base comprising two or more tracks, wherein at least one track is perpendicular to at least one other track;
a module for holding a rotary cutting tool, wherein the module is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track;
at least one module for holding a dowel, wherein the at least one module is configured to slide in the tracks in both parallel and perpendicular orientation to a rotary cutting tool module disposed in a track during use;
wherein the at least one module for holding a dowel includes a collet module comprising a base configured to slide in a track and a collet configured to hold a dowel such that an end of the dowel can contact the cutting tool during use; and
wherein the device comprises a support member comprising a threaded opening attached to the machine base in a track, and wherein the collet module comprises a threaded projection configured to threadably mate with the threaded opening such that turning the threaded projection is effective to move the collet module in the track.

35. A device for manufacturing a bone dowel comprising:
a machine base comprising two or more tracks, wherein at least one track is perpendicular to at least one other track;
a module for holding a rotary cutting tool, wherein the module is configured to slide in the tracks;
a collet module comprising a base configured to slide in a track in both parallel and perpendicular orientation to a rotary cutting tool module and a collet configured to hold a dowel by one end thereof;
a vise module comprising a base configured to slide in a track and a vise configured to hold a dowel along the length thereof;
a threading module comprising a base configured to slide in a track, a dead center, and a chuck opposed to the dead center; and
wherein the machine base comprises a support member comprising a threaded opening attached to the machine base in a track, and wherein the threading module comprises a threaded projection configured to threadably mate with the threaded opening such that turning the threaded projection is effective to move the threading module in the track, and to turn a dowel held in the threading module.

36. The device of claim 34, wherein the at least one module is configured to hold the dowel parallel to the base.

37. The device of claim 34, wherein the at least one module includes a vise module comprising a base configured to slide in a track and a vise configured to hold a dowel along the length thereof such that an end of the dowel can contact a cutting tool during use.

38. The device of claim 37, wherein the at least one module is configured to hold a dowel perpendicular to the base.

39. The device of claim 34, wherein the at least one module includes a threading module comprising a base configured to slide in a track, a dead center, and a chuck opposed to the dead center, configured such that the circumferential portion of a dowel held in the threading module can contact a cutting tool while rotating around the long axis of the dowel during use.

40. The device of claim 34, wherein the device comprises a support member attached to the machine base in a track, wherein the support member comprises a threaded opening.

41. The device of claim 35, wherein the device is autoclavable.

42. The device of claim 34, wherein the collet module comprises a knob attached to the threaded projection configured so that turning the knob turns the threaded projection.

43. The device of claim 34, wherein the collet module comprises a knob attached to the collet configured so that turning the knob turns the collet.

44. The device of claim 39, wherein the machine base comprises a support member comprising a threaded opening attached to the machine base in a track, and wherein the threading module comprises a threaded projection configured to threadably mate with the threaded opening, such that turning the threaded projection is effective to move the threading module in the track and to turn a dowel held in the threading module.

45. The device of claim 34, wherein the device is autoclavable.

46. The device of claim 34, further comprising a high speed rotary cutting tool.

47. A device for manufacturing a bone dowel comprising:
a machine base comprising two or more tracks, wherein at least one track is perpendicular to at least one other track;
a module for holding a rotary cutting tool, wherein the module is slidably disposed in a first track;
a support member comprising a threaded opening attached to the machine base in a second track in perpendicular orientation to the first track; and
a collet module for smoothing the ends of a dowel and for drilling center holes in the ends of a dowel, wherein the collet modules is slidable in both the first and second tracks and wherein the collet module comprises:
a base configured to slide in the tracks;
a threaded projection configured to threadably mate with the threaded opening;
a knob attached to the threaded projection, configured such that turning the knob turns the threaded projection;
a collet configured to hold a dowel by one end thereof; and
a knob attached to the collet configured such that turning the knob is effective to turn the collet.

48. The device of claim 47, wherein the module for holding a rotary cutting tool comprises an arm rigidly attached to the module and configured to threadably engage a threaded rod, wherein the rod is disposed parallel to the first track and is rotatable in one or more support members attached to the machine base such that turning the rod is effective to move the module in the track.

49. The device of claim 47, further comprising a high speed rotary cutting tool.

50. A device for manufacturing a bone dowel comprising:
   a machine base comprising two or more tracks, wherein at least one track is perpendicular to at least one other track;
   a module for holding a rotary cutting tool, wherein the module is disposed in a track and comprises an arm rigidly attached to the module and configured to threadably engage a threaded rod, wherein the rod is disposed parallel to the track and is rotatable in one or more support members attached to the machine base such that turning the rod is effective to move the module in the track;
   at least one module for holding a dowel, wherein the at least one module is configured to slide in the tracks in both parallel and perpendicular orientation to a rotary cutting tool module disposed in a track during use;
   wherein the at least one module for holding a dowel includes a collet module comprising a base configured to slide in a track and a collet configured to hold a dowel such that an end of the dowel can contact the cutting tool during use; and
   wherein the collet module comprises a knob attached to the collet configured so that turning the knob turns the collet.

51. The device of claim 50, wherein the device is autoclavable.

52. The device of claim 47, wherein the device is autoclavable.

53. A device for manufacturing a bone dowel comprising:
   a machine base comprising two or more tracks, wherein at least one track is perpendicular to at least one other track;
   a module for holding a rotary cutting tool, wherein the module is slidably disposed in a first track;
   a support member comprising a threaded opening attached to the machine base in a second track in perpendicular orientation to the first track; and
   a threading module for threading a dowel, wherein the threading module comprises:
      a base configured to slide in the tracks;
      a first support member disposed on a end of the base and providing an opening therethrough and a rod disposed in the opening and attached to a moveable member, wherein the rod projects through the moveable member to provide a dead center, and a spring disposed between the first support member and the moveable member configured to bias the moveable member away from the first support member;
      a second support member on the opposite end of the base from the first support member and providing an opening therethrough;
      a threaded projection disposed in the opening in the second support member and configured to threadably mate with the threaded opening;
      a chuck configured to hold an end of a dowel and attached to the threaded projection; and
      a knob attached to the threaded projection and to the chuck, configured such that turning the knob is effective to turn the threaded projection and the chuck.

54. The device of claim 53, wherein the module for holding a rotary cutting tool comprises an arm rigidly attached to the module and configured to threadably engage a threaded rod, wherein the rod is disposed parallel to the first track and is rotatable in one or more support members attached to the machine base such that turning the rod is effective to move the module in the track.

55. The device of claim 53, further comprising a high speed rotary cutting tool.

56. A device for manufacturing a bone dowel comprising:
   a machine base comprising two or more tracks, wherein at least one track is perpendicular to at least one other track;
   a module for holding a rotary cutting tool, wherein the module is disposed in a first track and comprises an arm rigidly attached to the module and configured to threadably engage a threaded rod, wherein the rod is disposed parallel to the first track and is rotatable in one or more support members attached to the machine base such that turning the rod is effective to move the module in the track;
   a support member comprising a threaded opening attached to the machine base in a second track in perpendicular orientation to the first track; and
   a collet module for smoothing the ends of a dowel and for drilling center holes in the ends of a dowel, wherein the collet module comprises:
      a base configured to slide in the tracks;
      a threaded projection configured to threadably mate with the threaded opening;
      a knob attached to the threaded projection, configured such that turning the knob turns the threaded projection;
      a collet configured to hold a dowel by one end thereof; and
      a knob attached to the collet configured such that turning the knob is effective to turn the collet.

57. The device of claim 56, further comprising a high speed rotary cutting tool.

58. The device of claim 53, wherein the device is autoclavable.

59. The device of claim 56, wherein the device is autoclavable.

60. A device for manufacturing a bone dowel comprising:
   a machine base comprising two or more tracks, wherein at least one track is perpendicular to at least one other track;
   a module for holding a rotary cutting tool, wherein the module is disposed in a first track and comprises an arm rigidly attached to the module and configured to threadably engage a threaded rod, wherein the rod is disposed parallel to the first track and is rotatable in one or more support members attached to the machine base such that turning the rod is effective to move the module in the track;
   a support member comprising a threaded opening attached to the machine base in a second track in perpendicular orientation to the first track; and
   a threading module for threading a dowel, wherein the threading module comprises:
      a base configured to slide in the tracks;
      a first support member disposed on a end of the base and providing an opening therethrough and a rod disposed in the opening and attached to a moveable member, wherein the rod projects through the moveable member to provide a dead center, and a spring disposed between the first support member and the moveable member configured to bias the moveable member away from the first support member;

a second support member on the opposite end of the base from the first support member and providing an opening therethrough;

a threaded projection disposed in the opening in the second support member and configured to threadably mate with the threaded opening;

a chuck configured to hold an end of a dowel and attached to the threaded projection; and a knob attached to the threaded projection and to the chuck, configured such that turning the knob is effective to turn the threaded projection and the chuck.

61. The device of claim 60, further comprising a high speed rotary cutting tool.

62. A device for manufacturing a bone dowel comprising:

a machine base comprising two or more tracks, wherein at least one track is perpendicular to at least one other track;

a module for holding a rotary cutting tool, wherein the module is slidably disposed in a first track;

a support member comprising a threaded opening attached to the machine base in a second track in perpendicular orientation to the first track;

a collet module for smoothing the ends of a dowel and for drilling center holes in the ends of a dowel, wherein the collet module comprises:
  a base configured to slide in the tracks;
  a threaded projection configured to threadably mate with the threaded opening;
  a knob attached to the threaded projection, configured such that turning the knob turns the threaded projection;
  a collet configured to hold a dowel by one end thereof, and
  a knob attached to the collet configured such that turning the knob is effective to turn the collet;

a vise module for machining a groove in an end of a dowel, wherein the vise module comprises:
  a base configured to slide in the tracks;
  a pair of opposed vise jaws including a mobile vise jaw and a stationary vise jaw;
  a knob attached to the mobile vise jaw by a rod, configured such that turning the knob is effective to move the mobile vise jaw along the top of the base; and a threading module for threading a dowel, wherein the threading module comprises:
  a base configured to slide in the tracks;
  a first support member disposed on a end of the base and providing an opening therethrough and a rod disposed in the opening and attached to a moveable member, wherein the rod projects through the moveable member to provide a dead center, and a spring disposed between the first support member and the moveable member configured to bias the moveable member away from the first support member;
  a second support member on the opposite end of the base from the first support member and providing an opening therethrough;
  a threaded projection disposed in the opening in the second support member and configured to threadably mate with the threaded opening;
  a chuck configured to hold an end of a dowel and attached to the threaded projection;
  a knob attached to the threaded projection and to the chuck, configured such that turning the knob is effective to turn the threaded projection and the chuck.

63. The device of claim 62, wherein the module for holding a rotary cutting tool comprises an arm rigidly attached to the module and configured to threadably engage a threaded rod, wherein the rod is disposed parallel to the track and is rotatable in one or more support members attached to the machine base such that turning the rod is effective to move the module in the track.

64. The device of claim 62, further comprising a high speed rotary cutting tool.

65. A device for manufacturing a bone dowel comprising:

a machine base comprising two or more tracks, wherein at least one track is perpendicular to at least one other track;

a module for holding a rotary cutting tool, wherein the module is disposed in a first track and comprises an arm rigidly attached to the module and configured to threadably engage a threaded rod, wherein the rod is disposed parallel to the first track and is rotatable in one or more support members attached to the machine base such that turning the rod is effective to move the module in the track;

a support member comprising a threaded opening attached to the machine base in a second track in perpendicular orientation to the first track;

a collet module for smoothing the ends of a dowel and for drilling center holes in the ends of a dowel, wherein the collet module comprises:
  a base configured to slide in the tracks;
  a threaded projection configured to threadably mate with the threaded opening;
  a knob attached to the threaded projection, configured such that turning the knob turns the threaded projection;
  a collet configured to hold a dowel by one end thereof; and
  a knob attached to the collet configured such that turning the knob is effective to turn the collet;

a vise module for machining a groove in an end of a dowel, wherein the vise module comprises:
  a base configured to slide in the tracks;
  a pair of opposed vise jaws including a mobile vise jaw and a stationary vise jaw;
  a knob attached to the mobile vise jaw by a rod, configured such that turning the knob is effective to move the mobile vise jaw along the top of the base; and a threading module for threading a dowel, wherein the threading module comprises:
  a base configured to slide in the tracks;
  a first support member disposed on a end of the base and providing an opening therethrough and a rod disposed in the opening and attached to a moveable member, wherein the rod projects through the moveable member to provide a dead center, and a spring disposed between the first support member and the moveable member configured to bias the moveable member away from the first support member;
  a second support member on the opposite end of the base from the first support member and providing an opening therethrough;
  a threaded projection disposed in the opening in the second support member and configured to threadably mate with the threaded opening;

a chuck configured to hold an end of a dowel and attached to the threaded projection; and a knob attached to the threaded projection and to the chuck, configured such that turning the knob is effective to turn the threaded projection and the chuck.

66. The device of claim 65, further comprising a high speed rotary cutting tool.

67. A device for manufacturing a bone dowel comprising:

a machine base comprising two or more tracks, wherein at least one track is perpendicular to at least one other track;

a module for holding a rotary cutting tool, wherein the module is disposed in a first track and comprises an arm rigidly attached to the module and configured to threadably engage a threaded rod, wherein the rod is disposed parallel to the first track and is rotatable in one or more support members attached to the machine base such that turning the rod is effective to move the module in the track;

a high speed rotary cutting tool;

a support member comprising a threaded opening attached to the machine base in a second track in perpendicular orientation to the first track;

a collet module for smoothing the ends of a dowel and for drilling center holes in the ends of a dowel, wherein the collet module comprises:

a base configured to slide in the tracks;

a threaded projection configured to threadably mate with the threaded opening;

a knob attached to the threaded projection, configured such that turning the knob turns the threaded projection;

a collet configured to hold a dowel by one end thereof; and a knob attached to the collet configured such that turning the knob is effective to turn the collet;

a vise module for machining a groove in an end of a dowel, wherein the vise module comprises:

a base configured to slide in the tracks;

a pair of opposed vise jaws including a mobile vise jaw and a stationary vise jaw;

a knob attached to the mobile vise jaw by a rod, configured such that turning the knob is effective to move the mobile vise jaw along the top of the base; and a threading module for threading a dowel, wherein the threading module comprises:

a base configured to slide in the tracks;

a first support member disposed on a end of the base and providing an opening therethrough and a rod disposed in the opening and attached to a moveable member, wherein the rod projects through the moveable member to provide a dead center, and a spring disposed between the first support member and the moveable member configured to bias the moveable member away from the first support member;

a second support member on the opposite end of the base from the first support member and providing an opening therethrough;

a threaded projection disposed in the opening in the second support member and configured to threadably mate with the threaded opening;

a chuck configured to hold an end of a dowel and attached to the threaded projection; and a knob attached to the threaded projection and to the chuck, configured such that turning the knob is effective to turn the threaded projection and the chuck.

68. The device of claim 60, wherein the device is autoclavable.

69. The device of claim 62, wherein the device is autoclavable.

70. The device of claim 63, further comprising a knob attached to the rod.

71. The device of claim 65, wherein the device is autoclavable.

72. The device of claim 67, wherein the device is autoclavable.

* * * * *